United States Patent
Hwang et al.

(10) Patent No.: US 9,579,261 B2
(45) Date of Patent: Feb. 28, 2017

(54) METHOD AND APPARATUS FOR PREPARING NOVEL LIPOSOME

(75) Inventors: Sung Joo Hwang, Seoul (KR); Hee Jun Park, Daejeon (KR); Wonkyung Cho, Jeonbuk (KR); Kwang-Ho Cha, Daejeon (KR); Junsung Park, Daejeon (KR); Chanhyuk Park, Gyeongsangnam-do (KR); Donggeon Gu, Daejeon (KR)

(73) Assignee: BCWORLD PHARM. CO., LTD., Gyeonggi-do (KR)

( * ) Notice: Subject to any disclaimer, the term of this patent is extended or adjusted under 35 U.S.C. 154(b) by 655 days.

(21) Appl. No.: 13/580,236

(22) PCT Filed: Feb. 24, 2011

(86) PCT No.: PCT/KR2011/001303
§ 371 (c)(1),
(2), (4) Date: Aug. 21, 2012

(87) PCT Pub. No.: WO2011/105835
PCT Pub. Date: Sep. 1, 2011

(65) Prior Publication Data
US 2013/0069261 A1    Mar. 21, 2013

(30) Foreign Application Priority Data

Feb. 24, 2010    (KR) .................... 10-2010-0016555

(51) Int. Cl.
*A61J 3/07*    (2006.01)
*A61K 9/127*    (2006.01)
(Continued)

(52) U.S. Cl.
CPC ................ *A61J 3/07* (2013.01); *A61K 9/127* (2013.01); *A61K 9/1277* (2013.01); *A61K 9/19* (2013.01);
(Continued)

(58) Field of Classification Search
CPC ...................................................... A61J 3/07
See application file for complete search history.

(56) References Cited

U.S. PATENT DOCUMENTS

| 4,766,046 A | 8/1988 | Abra et al. |
| 5,262,168 A * | 11/1993 | Lenk ............... A61K 9/127 |
| | | 264/4.3 |

(Continued)

FOREIGN PATENT DOCUMENTS

| CA | 2455597 A1 * | 2/2003 | ............. A61K 39/39 |
| CN | 1471908 A | 2/2004 | |

(Continued)

OTHER PUBLICATIONS

Locke, Supercritical CO2 Fluid Extraction of Fluometuron Herbicide from Soil, J. Agric. Food Chem., 1993, 41, 1081-1084.*

(Continued)

*Primary Examiner* — Jeffrey Washville
(74) *Attorney, Agent, or Firm* — Quarles & Brady, LLP

(57) ABSTRACT

Disclosed is a method for preparing a liposome formulation. In the disclosed method, a lipid fraction is dissolved in an organic solvent. The solution including a bioactive component and the lipid fraction, together with a carrier, is put in a reaction vessel, and a supercritical fluid is introduced thereto, so as to prepare particles coated with the bioactive component-lipid. The supercritical fluid is discharged by compression to obtain proliposome particles, and then the proliposome particles are hydrated by an aqueous solution including water so as to form a liposome solution. Preferably, the formulation may include one or more bioactive components. As required, the liposome formulation may be further processed by methods such as particle size reduction, removal of organic solvent, and freeze-drying. The preparation method can be easily carried out at a laboratory scale.

(Continued)

Furthermore, the same method can be employed in liposome formulation preparation in mass production, or at a commercial scale.

7 Claims, 2 Drawing Sheets

(51) Int. Cl.
*A61K 9/19* (2006.01)
*A61K 31/70* (2006.01)
*B01D 11/04* (2006.01)

(52) U.S. Cl.
CPC .......... *A61K 31/70* (2013.01); *B01D 11/0411* (2013.01)

(56) References Cited

U.S. PATENT DOCUMENTS

| | | | |
|---|---|---|---|
| 5,554,382 A * | 9/1996 | Castor | A61K 9/1277 264/4.1 |
| 2009/0068256 A1 * | 3/2009 | Meers | A61K 9/1272 424/450 |
| 2009/0155346 A1 * | 6/2009 | Winter et al. | 424/450 |

FOREIGN PATENT DOCUMENTS

| | | |
|---|---|---|
| JP | H09502644 A | 3/1997 |
| JP | 2003506479 A | 2/2003 |
| JP | 2005162702 A | 6/2005 |
| JP | 2008512233 A | 4/2008 |
| JP | 2009051842 A | 3/2009 |
| KR | 1019960702748 A | 5/1996 |
| WO | 8701933 A1 | 4/1987 |

OTHER PUBLICATIONS

Shah, et al., Liposomal Amphotericin B Dry Powder Inhaler: Effect of Fines on in Vitro Performance, Pharmazie, 2004, 59:812-813.

European Patent Office, Supplementary European Search Report, EP 11747725, Apr. 22, 2014, 5 pages.

Canadian Intellectual Property Office, Office Action, CA 2,789,320, May 15, 2014, 2 pages.

Hwang, et al., In Vitro Skin Permeation of Nicotine from Proliposomes, Journal of Controlled Release, 1997, 49:177-184.

Japan Patent Office, Notification of Reasons for Refusal, Application No. 2012-554934, Dec. 10, 2013, 6 pages.

Bridson, et al., The Preparation of Liposomes Using Compressed Carbon Dioxide: Strategies, Important Considerations and Comparison with Conventional Techniques, Journal of Pharmacy and Pharmacology, 2006, 58:775-785.

Kadimi, et al., In Vitro Studies on Liposomal Amphotericin B Obtained by Supercritical Carbon Dioxide-Mediated Process, Nanomedicine: Nanotechnology, Biology and Medicine, 2007, 3:273-280.

Canadian Intellectual Property Office, Examination Report, Application No. 2,789,320, Jun. 19, 2013, 4 pages.

International Search Report, PCT/KR2011/001303, Nov. 24, 2011.

Hwang, et al., In Vitro Skin Permeation of Nicotine from Proliposomes, Journal of Controlled Release, 1997, 49 (2-3):177-184, Abstract.

Notice of Allowance, Korean Patent Application No. 10-2010-0016555, Dec. 29, 2011.

Database WPI Week 200430 Thomson Scientific, London, GB; AN 2004-317306 XP002723320, & CN 1 471 908 A (Xie T) Feb. 4, 2004.

The State Intellectual Property Office of China, First Office Action, Application No. 201180011038.3, Apr. 17, 2013.

English Excerpt of Citation 1: Xie, The Experimental Study of Preparing Low-Water-Soluble Drugs Liposomes with the Supercritical Technology, [The full text database of the Chinese outstanding master's dissertation Medicine Health Science and Technology Series], 2009 (10), E079-44.

English Excerpt of Citation 2: Li, Research Progress of Chinese Medicine Liposomes Targeted Drug Delivery, The Journal of Liaoning Medical University, 2009, vol. 30(1).

* cited by examiner

METHOD AND APPARATUS FOR PREPARING NOVEL LIPOSOME

CROSS-REFERENCE TO RELATED APPLICATIONS

This application represents the national stage entry of PCT International Application No. PCT/GB2011/050242 filed Feb. 10, 2011, which claims the benefit of Great Britain Application 1002223.4, filed Feb. 10, 2010, both of which are hereby incorporated herein by reference for all purposes.

TECHNICAL FIELD

The present invention relates to a novel method for preparing liposome, and an apparatus for preparing the liposome, and preferably the liposome formulation may include one or more bioactive components. More particularly, the present invention relates to a method and an apparatus for preparing liposome formulation, in which the liposome formulation has stability against bioactive components, and formulation stability, and can be mass-produced with a high yield.

BACKGROUND ART

A liposome is a vesicle including phospholipids and their derivatives. It spontaneously forms a vesicle when phospholipids and their derivatives are dispersed in water, and has a characteristic of a lipid bilayer which includes an aqueous nucleus therewithin. Various liposomes have been used as carriers for drugs, enzymes, and therapeutic agents such as gene sequences in medical, pharmacy, and biochemistry fields.

Examples of liposome compositions are disclosed in U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627,218; US Patent Publication Nos 2003/0224037; 2004/0022842; 2001/0033860; 2003/0072794; 2003/0082228; 2003/0212031; 2003/0203865; 2004/0142025; 2004/0071768; International Patent Publication Nos WO 00/74646; WO 96/13250; WO 98/33481; Papahadjopolulos D, Allen T M, Gbizon A, et al. "Sterically stabilized liposomes: Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556.

Various methods for preparing liposome have been known in the technical fields of the present invention, and some of them are described in detail in Liposome Technology 2nd Edition in G. Gregoriadis, CRC Press Inc., Boca Raton (1993).

In a case of these conventional liposome preparation technologies, it is possible to effectively prepare liposome at a small laboratory-scale manufacturing scale. However, the technologies have a large problem in that at a large commercial manufacturing scale, it is impossible to effectively mass-produce liposome due to some problems such as removal of an organic solvent used for dissolving phospholipids, and a size of a reactor for forming a lipid membrane.

As one of liposome preparing methods for commercial-scale mass-production, US Patent Publication No. 2004/0175417 discloses a method for preparing liposome, in which a complex of amphotericin B and phospholipids is formed in a mixed solution of oxidized chloroform and methanol, and then is spray-dried so as to provide lipid powder. However, this technology has a large problem in that high-boiling point solvents, such as dimethyacetamide (DMA), dimethylformamide (DMF), dimethylsulfoxide (DMSO), cannot be employed in a process because heated air is used for removing an organic solvent during a thyspray process. The above mentioned solvents such as DMA, DMF and DMSO are generally known to sufficiently dissolve amphotericin B and maintain the stability of the dissolved amphotericin B.

DISCLOSURE OF INVENTION

Technical Problem

Therefore, the present inventors have continuously conducted research on the development of a new method for mass-producing a liposome formulation. As a result, they have completed the present invention, in view of the fact that a liposome solution obtained by preparing proliposome through a supercritical fluid and hydrating the proliposome has a high content, a high loading efficiency, and a high stability of a bioactive component, and can be mass-produced by a simple apparatus.

Accordingly, an object of the present invention is to provide a preparation method for mass-producing liposome formulation, in which the liposome formulation has a high content, a high loading efficiency, and a high stability of a bioactive component, and high formulation stability.

Another object of the present invention is to provide a liposome preparation apparatus for mass-producing liposome formulation, in which the liposome formulation has a high content, a high loading efficiency, and a high stability of a bioactive component, and high formulation stability.

Solution to Problem

In accordance with an aspect of the present invention, there is provided a method for preparing liposome formulation, the method including the steps of: (a) dissolving a lipid fraction including at least one kind selected from phospholipid or sterol, and a bioactive substance (drug) in an organic solvent; (b) putting the organic solvent solution including the lipid fraction together with a saccharide carrier into a reaction vessel, and introducing a supercritical fluid thereto so as to prepare drug-lipid coated particles (to be formed into liposome, hereinafter, referred as "proliposome particles"; (c) discharging the supercritical fluid by compression so as to obtain proliposome particles; and hydrating the proliposome particles by an aqueous solution including water so as to form liposome.

Meanwhile, the method may further include the steps of sterile-filtrating the liposome formulation; and/or freeze-drying the liposome formulation.

<The Preparation Sequence of Liposome of the Present Invention>

In accordance with another aspect of the present invention, there is provided an apparatus for performing the liposome formulation preparation method, the apparatus including: a reaction vessel in which the step of preparing proliposome particles and the step of forming a liposome solution are carried out; a supercritical fluid storage vessel for receiving a supercritical fluid; a supercritical fluid supplying tube for transporting the supercritical fluid to the reaction vessel from the supercritical fluid storage vessel, which is connected from the supercritical fluid storage vessel to the reaction vessel; a supercritical fluid supply amount adjusting pump for controlling an amount of the transported supercritical fluid, which exists in the supercritical fluid supplying tube; a reactive material introducing part for providing a reactive material to the reaction vessel, which is connected to the inside of the reaction vessel; a pressure meter for measuring a pressure in the reaction vessel, which is connected to the inside of the reaction vessel; a supercritical fluid discharging tube for discharging the supercritical fluid, which is connected to the reaction vessel; a pressure-reducing valve for discharging the supercritical fluid, which exists in the supercritical fluid discharging tube; and a back pressure valve for discharging the supercritical fluid while maintaining a predetermined pressure or more, which exists in the supercritical fluid discharging tube.

Hereinafter, the present invention will be described in more detail. In the method for preparing liposome formulation, according to the present invention, a lipid fraction is dissolved in an organic solvent, and the mixed solution, together with a carrier, is put in a reaction vessel. Then, a supercritical fluid is introduced thereto so as to form proliposome particles. The supercritical fluid is discharged by compression to obtain proliposome particles, and then the proliposome particles are hydrated by an aqueous solution including water so as to form a liposome solution.

In a lipid fraction constituting the liposome, a phospholipid may be selected from the group including phosphatidylglycerols, phosphatidylcholines, phosphatidylethanolamines, phosphatidylserines, phosphatidylinositols, yolk lecithin, soybean lecithin, N-[1-(2,3-Dioleoyloxy)propyl]-N,N,N-trimethylammonium methylsulfate (DOTAP), N-[1-(2,3-dioleyloxy)propyl]-N,N,N-trimethylammonium chloride (DOTMA), dioctadecyldimethylammonium bromide (DODAB), 2,3-dioleyloxy-N-[2(sperminecarboxamido) ethyl]-N,N-dimethyl-1-propanaminium trifluoroacetate (DOSPA), dioleoyl phosphatidylethanolamine (DOPE), 1,2-dimyristyloxypropyl-3-dimethyl-hydroxy ethyl ammonium bromide (DMRIE), didodecyldimethylammonium bromide (DDAB), 3β-[N—(N',N'-dimethylaminoethane)-carbamoyl] cholesterol (DC-Chol), dioctadecylamidoglycylspermine (DOGS), N,N-[bis(2-hydroxyethyl)]-N-methyl-N-[2,3-di(tetradecanoyloxy)propyl]ammonium iodide, [N,N,N',N'-tetramethyl-N,N'-bis(2-hydroxyethyl)-2,3-di(oleoyloxy)-1,4-butanediamm onium iodide], diethylaminoethyl cellulose (DEAE-C), N,N,N,N-tetramethyl-N,N,N,N-tetrapalmitylspermine, dioleoyl phosphatidylethanolamine, N-t-butyl-N'-tetradecyl-3-tetradecylaminopropionamidine, and diethylaminoethyl dextran (DEAE-D), but is not limited thereto. Also, the above mentioned phospholipids may be used in combination. Further, such a phospholipid include commercially available reagents from a variety of sources, and include but are not limited to, for example, Lipofect ACE (Life Technologies), Lipofection (Life Technologies), LipofectAmine (Life Technologies), CeliFectin (Life Technologies), DMRIE-C(Life Technologies), DDAB (Sigma), DC-Chol (Sigma), DOTAP (Boehringer Mannheim, Avanti Polar Lipids, Biontex), MRX-230 (Avanti Polar Lipids), MRX-220 (Avanti Polar Lipids), Transfectam (Promega), Transfast (Promega), Tfx 10 (Promega), Tfx 20 (Promega), Tfx 50 (Promega), Prefection-CaPO4 (Promega), Prefection-DEAE-Dextran (Promega), GeneSHUTTLE-40 (Quantum Biotechnologies), CLONfectin (Clontech), METAFECTENE (Biontex), INSECTOGENE (Biontex), Effectene (Qiagen), FuGENE 6 (Roche Molecular Biochemicals), GENESEAL (MTTI). The phosphatidyl glycerols may include distearoyl phosphatidyl glycerol, dipalmitoyl phosphatidyl glycerol, and other possible phosphatidyl glycerol derivatives.

In a lipid fraction constituting the liposome, a sterol may be selected from the group including cholesterol, cholesterol hexasuccinate, ergosterol, lanosterol, and combinations thereof, but is not limited thereto. Preferably, cholesterol may be used.

A solvent for preparing the organic solvent including the lipid fraction is divided into a bioactive-component dissoluble solvent and a lipid-fraction dissoluble solvent. The bioactive-component dissoluble solvent may be selected from the group including dimethylacetamide, dimethylformamide, dimethylsulfoxide, methanol, ethanol, and combinations thereof, but is not limited thereto. Preferably, dimethylacetamide may be used. The lipid-fraction dissoluble solvent may be selected from the group including chloroform, methanol, ethanol, ether, and combinations thereof, but is not limited thereto. Preferably, a mixture of methanol and chloroform may be used. Also, it is preferable that when a bioactive component solution is mixed with a lipid fraction solution, precipitation does not occur. The solvent is a component to be removed by a supercritical fluid later, and is preferably used in a minimum amount so as to reduce a process time of an organic solvent removing step.

The bioactive component is a physiological active substance, which may be one or more selected from the group including autonomic nerve modulators, corticosteroids, diuretics, analgesics, sex hormones, anesthetics, anthelminitics, antihistamines, antiprotozoal agents, antianemics, cardiovascular disease agents, antianxiety agents, antiasthmatics, anticonvulsants, antidepressants, antidiabetics, antidiuretics, antidotes, antiepileptics, antifungal agents, antihyperlipidemic agents, antihyperlipoproteinemics, antihypertensives, antihypotensives, antibiotics, analgesics, antimigraines, antimycotics, antinauseants, anticancer agents, antidepressants, antiparkinsonians, antpsoriatics, neuropsychiatric agents, antiplatelet agents, antitussive expectorant agents, anti-ulceratives, bronchodilators, cardiotonics, diuretics, emetics, anti-ulceratives, hormones, immunomodulators, muscle relaxants, neuroleptics, vasodilators, antivirals, insecticides, protein drugs, gene drugs and antibodies.

In the step of preparing the bioactive component solution, according to a conventional method known in the art, an acidic or alkaline component may be added in a small amount in consideration of the chemicophysical properties of the bioactive component so as to increase the solubility. In an acidic condition, when the solubility is increased, an acid such as ascorbic acid, hydrochloric acid, or acetic acid may be added in a small amount. Then, after the addition of the acid, a base, such as sodium hydroxide, may be added for neutralization. In the same manner, in a basic condition, when the solubility is increased, a basic material such as alkaline metal may be added and dissolved. Then, acid may be added for neutralization.

As the saccharide carrier, lactose, sucrose, maltose, trehalose, dextrose, sorbitol, mannitol, xylitol, or a combination thereof may be used, but the present invention is not limited thereto. Preferably, lactose may be used. Such a saccharide may not only perform a role as a carrier, but also perform a role of stabilizing a physical structure of liposome during the liposome's freeze-drying for convenience of storage after preparation of the liposome through hydration.

As the supercritical fluid, supercritical carbon dioxide, supercritical nitrogen monoxide, supercritical acetylene, supercritical trifluoromethane, supercritical propane, supercritical ethylene, supercritical chlorofluocarbon or supercritical xenon may be used, but the present invention is not limited thereto.

In the step of preparing the proliposome particles, a predetermined time is required until the supercritical fluid and the organic solvent are mixed and reaches an equilibrium state. The required time may be in a range of about 1 to 30 minutes according to the amount of samples. The reaction in the step may be performed at a temperature and a pressure higher than those for maintaining the supercritical fluid state. When supercritical carbon dioxide is used as the supercritical fluid, a pressure is in a range of 120 to 300 bar, and is preferably 150 bar, and a temperature is in a range of 35 to 70° C., and is preferably 45° C. Also, in order to facilitate the mixing during the reaction, an agitating device may be used and continuously carry out the mixing. The rotation speed of the agitator is preferably in a range of 200 to 500 rpm. It is possible to determine if the reaction reaches the equilibrium state based on a point of time when the mixture of the supercritical fluid and the organic solvent reaches a homogenous state.

In order to remove the organic solvent remaining after the reaching of the equilibrium, a step for supplying an additional supercritical fluid is performed. The supply speed of the supercritical fluid is appropriately in a range of 5 to 20 ml/min. During this step, a predetermined pressure and a predetermined temperature are maintained in such a manner that the supercritical state within a reaction vessel can be maintained. The time required for this step may be in a range of about 10 minutes to 1 hour according to the amount of the organic solvent. Also, the supercritical fluid has an advantage in that it can easily remove not only a volatile organic solvent but also a non-volatile organic solvent (such as dimethylacetamide, dimethylformide, dimethylsulfoxide) having a difficulty in being removed by a conventional method.

After the organic solvent is completely removed, a step for discharging the supercritical fluid by decompression is performed in order to obtain proliposome particles. The decompression speed is appropriately in a range of 10 to 200 bar/min. It has to be noted that there is no loss of the proliposome particles during a decompression process. Also, there is an advantage in that sterilization is carried out while a high pressure is maintained and the decompression is performed.

In order to form the obtained proliposome particles into a liposome solution, a process for hydrating the particles into an aqueous solution may be optionally performed by including water at a phase transition temperature or more. The volume of the aqueous solution is appropriately in a range of 5 to 20 ml, and the temperature of the aqueous solution is appropriately in a range of 45 to 95° C., preferably of 65 to 80° C. Through this process, a drug-lipid film as a thin film formed on a carrier surface, in an aqueous solution at a phase transition temperature or more, forms a liposome in the same principle as that of a liquid thin film method. In general, the drug-lipid film has a wider surface area than the liquid thin film method and thus forms smaller and more uniform liposome particles after the hydration.

The prepared liposome may be optionally passed through a microfluidizer so as to reduce a particle size. The time required for this process is appropriately in a range of 1 to 10 minutes, and the temperature is appropriately in a range of 45 to 95° C., preferably of 65 to 85° C.

The prepared liposome may be optionally freeze-dried for convenience of storage. The saccharide used as a carrier in the preparation of the proliposome may stabilize the physical structure of liposome during freeze-drying by being dissolved in an aqueous solution including water during hydration. As the saccharide carrier, maltose, lactose, sucrose, trehalose, dextrose, sorbitol, mannitol, xylitol, or a combination thereof may be used, but the present invention is not limited thereto. Preferably, lactose may be used. Cake, plaque, or powder, which is formed by freeze-drying a liposome solution, may be administered through reconstitution by sterilized water when used.

The liposome formulation prepared according to the present invention may be used for parental injections, and transdermal, nasal, and inhalant drug delivery. A technology required for such formulation, and pharmaceutically acceptable carriers and additives are widely known to people skilled in the pharmaceutical field, and may refer to Remington's Pharmaceutical Sciences (19th ed., 1995).

According to another aspect of the present invention, an apparatus for preparing liposome according to the present invention includes: a reaction vessel in which the step of preparing proliposome particles and the step of forming a liposome solution are carried out; a supercritical fluid storage vessel for receiving supercritical fluid; a supercritical fluid supplying tube for transporting the supercritical fluid to the reaction vessel from the supercritical fluid storage vessel, which is connected from the supercritical fluid storage vessel to the reaction vessel; a supercritical fluid supply amount adjusting pump for controlling the amount of the transported supercritical fluid, which exists in the supercritical fluid supplying tube; a reactive material introducing part for providing a reactive material to the reaction vessel, which is connected to the inside of the reaction vessel; a pressure meter for measuring a pressure in the reaction vessel, which is connected to the inside of the reaction vessel; a supercritical fluid discharging tube for discharging the supercritical fluid, which is connected to the reaction vessel; a pressure-reducing valve for discharging the supercritical fluid, which exists in the supercritical fluid discharging tube; and a back pressure valve for discharging the supercritical fluid while maintaining a predetermined pressure or more, which exists in the supercritical fluid discharging tube.

In the apparatus, preferably, an agitating device exists within the reaction vessel, and the reaction vessel may include an agitator in itself or at the outside thereof so that the agitating device within the reaction vessel can mix reactive materials through rotation.

A mimetic diagram of the liposome preparing apparatus, according to one embodiment of the present invention, is shown in FIG. 1. The method for preparing amphotericin B containing liposome by using the apparatus according to one embodiment of the present invention, as shown in FIG. 1, will be described in Examples below.

The apparatus for performing the liposome preparing method of the present invention, as shown in FIG. 1, has a much simpler structure than a conventional liposome preparing apparatus using a supercritical fluid (U.S. Pat. No. 5,776,486), and thus can more conveniently and more economically perform the liposome preparing method.

Advantageous Effects of Invention

As described above, according to the method of the present invention, it is possible to prepare liposome which has a high content, a high loading efficiency, and a high stability of a bioactive component, and high formulation stability of liposome. Also, the method for preparing liposome formulation, according to the present invention, can be carried out by a simple apparatus due to a highly simplified process, and can be easily carried out at a laboratory scale. Furthermore, the same method can be employed in mass production, resulting in high economical efficiency.

BRIEF DESCRIPTION OF DRAWINGS

The foregoing and other objects, features and advantages of the present invention will become more apparent from the following detailed description when taken in conjunction with the accompanying drawings in which.

EXPLANATION OF SYMBOLS

Figure 1:
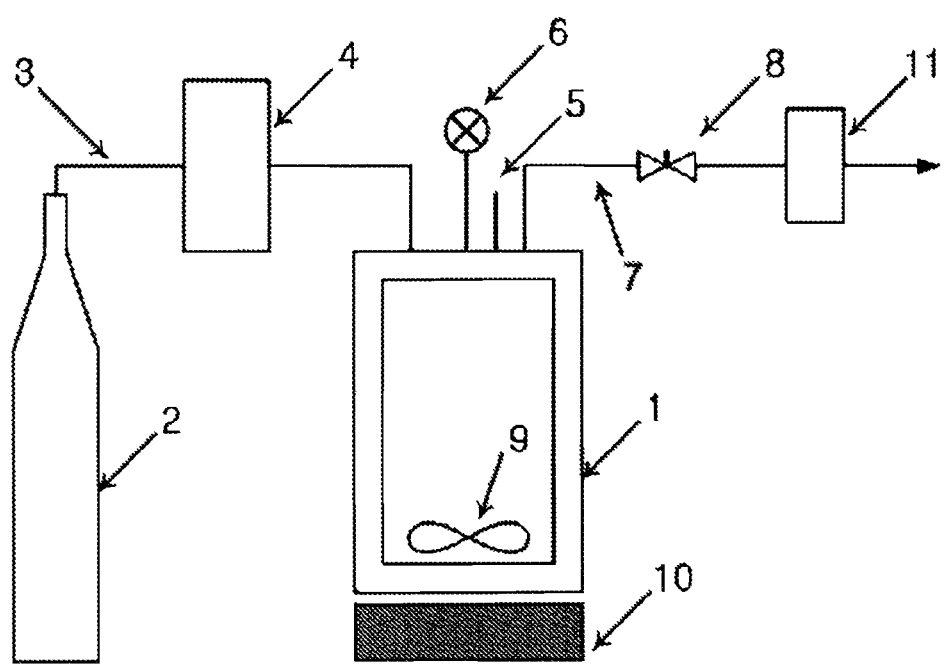
FIG. 1 is a mimetic diagram illustrating an apparatus for preparing amphotericin B-containing Liposome, according to one embodiment of the present invention.
Figure 2:
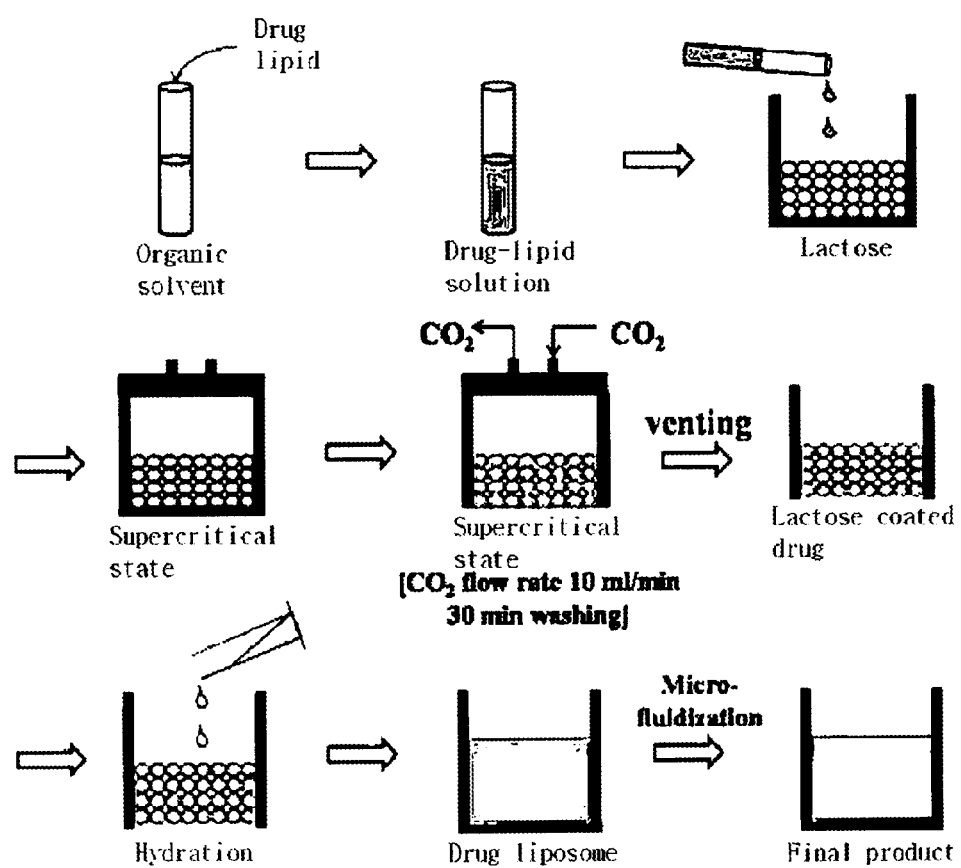
FIG. 2 is a schematic diagram illustrating the method for preparing liposomes according to one embodiment of the present invention.

1: reaction vessel
2: fluid storage vessel
3: supercritical fluid supplying tube
4: supercritical fluid supply amount adjusting pump
5: reactive material introducing part
6: pressure meter
7: supercritical fluid discharging tube
8: pressure-reducing valve
9: magnetic bar
10: magnetic agitator
11: back pressure regulator

MODE FOR THE INVENTION

Hereinafter, the present invention will be described in more detail with reference to Examples below. However, the Examples do not limit the scope of the present invention in any way but are only to help the understanding of the present invention.

Examples 1a to 1f and 2a to 2d

Preparation of Amphotericin B Liposome 84 mg of distearoyl phosphatidylcholine (DSPC) was dissolved in 1 ml of a 1:1 mixed solvent of chloroform and methanol at 65° C. 200 mg of ascorbic acid (VIt-C) was completely dissolved in 2 ml of N,N-dimethylacetamide (DMA) through ultrasonication for 10 minutes. 50 mg of amphotericin B was dissolved in the DMA-Vit C solution at 65° C., and the resulting solution was added with the DSPC solution. 213 mg of hydrogenated soybean phosphatidyl choline and 52 mg of cholesterol were dissolved in 1 ml of a 1:1 mixed solvent of chloroform and methanol at 65° C. The solution of hydrogenated soybean phosphatidyl choline and cholesterol was mixed with the amphotericin B-DSPG solution.

The amphotericin B-lipid solution and 900 mg of lactose were received in a reaction vessel 1, followed by sealing. The temperature of the reaction vessel was maintained at 45, 55, and 65° C. Through the operation of a pump 4, supercritical carbon dioxide was injected from a gas storage vessel 2 to the reaction vessel 1 via a supercritical fluid supplying tube 3, and then a pressure meter 6 was used to maintain the pressure at 150, 200, 250, and 300 bar. Through the operation of an agitator 10, the reaction vessel was rotated for 40 minutes at 500 rpm, while the materials were mixed up to an equilibrium state. To the reaction vessel, additional supercritical carbon dioxide was injected so as to remove the remaining organic solvent. Then, the supercritical carbon dioxide was discharged through a supercritical fluid discharging tube 7 by opening a pressure-reducing valve 8 while the reaction vessel was gradually decompressed to atmospheric pressure. After the decompression, from the reaction vessel, lactose particles coated with drugs and lipids were obtained. The particles were added with an aqueous solution (including 10 ml of water) at 55, 65, 75, and 85° C., and were agitated for 30 minutes, so as to provide a liposome solution.

The particle size of the liposome obtained as described above was measured by an electrophoretic light scattering spectrophotometer (ELS-8000), and the drug content was measured. The results of the Examples are shown as below.

Example 1 relates to the characteristics of a liposome solution according to a temperature and a pressure of a reaction vessel in a supercritical process. Particle sizes and drug contents according to temperatures and pressures of the reaction vessels, in Examples 1a to 1f, are noted in Table 1. Example 2 relates to the characteristics of a liposome solution according to a hydration temperature when proliposome particles prepared at a reaction temperature of 45° C. and a pressure of 200 bar are hydrated by addition of an aqueous solution (including water) in a supercritical process corresponding to Example 1a. Particle sizes, drug contents, and formation/non-formation of liposome according to hydration temperatures in Examples 2a to 2d are noted in Table 2.

TABLE 1

Particle sizes and drug contents according to temperatures and pressures of the reaction vessels, in Examples 1a to 1f,

| Example 1 | Reaction vessel in a supercritical process | | Particle size(nm) | Drug content(%) |
|---|---|---|---|---|
| | Temperature(° C.) | Pressure(bar) | | |
| a | 45 | 200 | 949.3 | 90.5 |
| b | 55 | 200 | 801.6 | 86.3 |
| c | 65 | 200 | 839.1 | 77.1 |
| d | 45 | 150 | 761.0 | 91.1 |
| e | 45 | 250 | 855.7 | 84.2 |
| f | 45 | 300 | 821.3 | 79.7 |

TABLE 2

Particle sizes, drug contents, and formation/non-formation of liposome according to hydration temperatures in Examples 2a to 2d

| Example 2 | Hydration temperature(° C.) | Particle size(nm) | Drug content(%) | etc |
|---|---|---|---|---|
| a | 55 | N/A | N/A | Non Formation of liposome |
| b | 65 | 949.3 | 90.5 | Formation of liposome |
| c | 75 | 866.2 | 88.1 | Formation of liposome |
| d | 85 | 752.1 | 84.3 | Formation of liposome |

Experimental Example 1

Stability of Amphotericin B Containing Liposome Against Freeze-Drying

In order to improve ease of storage of amphotericin B containing liposome according to the present invention, freeze-drying was carried out, and the stability was tested.

From among the example conditions, liposome, which was prepared by preparing proliposome at 45° C. and 200 bar, and carrying out hydration at 65° C., was passed through a microfluidizer so as to reduce the particle size of the liposome. Then, the liposome was freeze-dried, and was reconstituted by using distilled water as a redispersion solution. Before and after the freeze-drying, the size, the zeta potential, the drug content, and the loading efficiency of each liposome were measured. The result is noted in brief in Table 3.

TABLE 3

Before and after the freeze-drying, the size, the zeta potential, the drug content, and the loading capacity of each liposome

| state | Particle size(nm) | Zeta potential | Drug content(%) | Loading capacity(%) |
|---|---|---|---|---|
| Before freeze-drying | 137.35 | −42.49 | 91.6 | 89.2 |
| After freeze-drying | 146.85 | −43.64 | 90.2 | 83.5 |

According to the result, the liposome prepared by a supercritical process can maintain the average size, the zeta potential, the drug content, and the loading efficiency even after freeze-drying, and thus liposome formulation can be preserved for a long time by using freeze-drying.

INDUSTRIAL APPLICABILITY

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method for preparing liposome formulation, the method comprising the steps of:
   (a) dissolving a lipid fraction comprising at least one kind selected from phospholipid and sterol, and a bioactive substance in an organic solvent;
   (b) putting an organic solvent solution of the step (a) together with a saccharide carrier into a reaction vessel and preparing proliposome particles coated with a lipid-bioactive substance mixture by introducing a supercritical fluid thereto, wherein the supercritical fluid and the organic solvent solution of step (a) are mixed together until reaching equilibrium, wherein, after reaching equilibrium, an additional supercritical fluid is added, the saccharide carrier comprising one or more components selected from the group consisting of lactose, sucrose, maltose, trehalose, dextrose, sorbitol, mannitol, and xylitol;
   (c) discharging the supercritical fluid in step (b) by decompression so as to obtain the proliposome particles; and
   (d) hydrating the proliposome particles in step (c) by an aqueous solution comprising water at a temperature in the range of 65 to 95° C. so as to form a liposome solution,
   wherein the organic solvent including the lipid fraction is divided into a bioactive-component dissoluble solvent and lipid-fraction dissoluble solvent and the bioactive-component dissoluble solvent is at least one kind selected from the group consisting of dimethylacetamide, dimethylformamide and dimethylsulfoxide, and wherein the bioactive substance is amphotericin B.

2. A method as claimed in claim 1, further comprising the step of reducing a liposome particle size by passing the liposome solution in step (d) through a microfluidizer.

3. A method as claimed in claim 1, wherein the phospholipid is at least one kind selected from the group including phosphatidyl glycerols, phosphatidyl cholines, phosphatidyl ethanolamines, phosphatidylserines, phosphatidylinositols, yolk lecithin, soybean lecithin, N-[1-(2,3-Dioleoyloxy)propyl]-N,N,N-trimethylammonium methylsulfate (DOTAP), N-[1-(2,3-dioleyloxy)propyl]-N,N,N-trimethylammonium chloride (DOTMA), dioctadecyldimethylammonium bromide (DODAB), 2,3-dioleyloxy-N [2(sperminecarboxamido)ethyl]-N,N-dimethyl-1-propanaminium trifluoroacetate (DOSPA), dioleoyl phosphatidylethanolamine (DOPE), 1,2-dimyristyloxypropyl-3-dimethyl-hydroxy ethyl ammonium bromide (DMRIE), didodecyldimethylammonium bromide (DDAB), 3β-[N—(N',N'-dimethylaminoethane)-carbamoyl]cholesterol (DC-Chol), dioctadecylamidoglycylspermine (DOGS), N,N-[bis(2-hydroxyethyl)]-N-methyl-N-[2,3-di(tetradecanoyloxy)propyl] ammonium iodide, [N,N,N',N'-tetramethyl-N,N'-bis(2-hydroxyethyl)-2,3-di(oleoyloxy)-1,4-butanediammonium iodide], diethylaminoethyl cellulose (DEAE-C), N,N,N,N-tetrameth N,N,N,N-tetrapalmitylspermine, dioleoyl phosphatidylethanolamine, N-t-butyl-N'-tetradecyl-3-tetradecylaminopropionamidine, and diethylaminoethyl dextran (DEAE-D).

4. A method as claimed in claim 1, wherein the sterol is at least one kind selected from the group including cholesterol, cholesterol hexasuccinate, ergosterol, and lanosterol.

5. A method as claimed in claim 1, wherein the supercritical fluid is selected from the group including supercritical carbon dioxide, supercritical nitrogen monoxide, supercritical acetylene, supercritical trifluoromethane, supercritical propane, supercritical ethylene, supercritical chlorofluocarbon and supercritical xenon.

6. A method as claimed in claim 1, further comprising the step of sterile-filtrating the prepared liposome.

7. A method as claimed in claim 1, further comprising the step of freeze-drying the prepared liposome.

* * * * *